United States Patent [19]

Heeres et al.

[11] Patent Number: 5,254,553
[45] Date of Patent: Oct. 19, 1993

[54] 4-[4-[4-(4-HYDROXYPHENYL)-1-PIPERAZINYL]-PHENYL]-5-METHYL-3H-1,2,4-TRIAZOL-3-ONE DERIVATIVES

[75] Inventors: Jan Heeres, Vosselaar; Joseph H. Mostmans, Antwerpen; Johan R. M. Beetens, Zandhoven, all of Belgium

[73] Assignee: Janssen Pharmaceutica N.V., Beerse, Belgium

[21] Appl. No.: 933,848

[22] Filed: Aug. 24, 1992

[30] Foreign Application Priority Data

Sep. 13, 1991 [EP] European Pat. Off. ........ 91202351.2

[51] Int. Cl.⁵ .................. A61K 31/495; C07D 403/10
[52] U.S. Cl. ..................................... 514/252; 544/366
[58] Field of Search ........................ 544/366; 514/252

[56] References Cited

U.S. PATENT DOCUMENTS 4,791,111 12/1988 Heeres et al. ...................... 514/252
4,931,444 6/1990 Van Wauwe et al. ............... 514/252

Primary Examiner—Patricia L. Morris
Attorney, Agent, or Firm—Charles J. Metz

[57] ABSTRACT

2-[2-(4-chlorophenyl)-2-(hydroxy or oxo)ethyl]-2,4-dihydro-4-[4-[4-(4-hydroxyphenyl)-1-piperazinyl]-phenyl]-5-methyl-3H-1,2,4-triazol-3-one having the formula

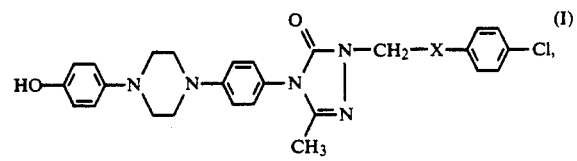

wherein X represents C=O or CHOH, for use as 5-lipoxygenase inhibitors. Pharmaceutical compositions, processes for preparing said compounds and compositions; and a method of treating leukotriene mediated diseases.

10 Claims, No Drawings

4-[4-[4-(4-HYDROXYPHENYL)-1-PIPERAZINYL]-PHENYL]-5-METHYL-3H-1,2,4-TRIAZOL-3-ONE DERIVATIVES

BACKGROUND OF THE INVENTION

In U.S. Pat. No. 4,791,111 there are described a number of 4-(4-phenyl-1-piperazinyl)phenol derivatives as intermediates for the preparation of compounds having antifungal properties. Subsequently, said intermediates and related derivatives known from U.S. Pat. No. 4,267,179 and U.S. Pat. No. 4,619,931 were described in U.S. Pat. No. 4,931,444 as 5-lipoxygenase inhibitors. Unexpectedly, it has now been found that with the compounds of the present invention superior plasma levels can be attained with respect to prior known compounds with an analogous structure.

DESCRIPTION OF THE INVENTION

The present invention is concerned with the 5-lipoxygenase inhibiting compound 2-[2-(4-chlorophenyl)-2-(hydroxy or oxo)ethyl]-2,4-dihydro-4-[4-[4(4-hydroxyphenyl)-1-piperazinyl]phenyl]-5-methyl-3H-1,2,4-triazol-3-one having the formula

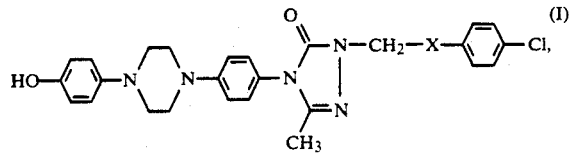

the pharmaceutically acceptable acid addition salts and the enantiomeric forms thereof, wherein X represents C=O or CHOH.

The compounds of formula (I) have basic properties and, consequently, they may be converted to their therapeutically active non-toxic acid addition salt forms by treatment with appropriate acids such as, for example, inorganic acids, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The term acid addition salt as used hereinabove also comprises the solvates which the compounds of formula (I) are able to form and said solvates are meant to be included within the scope of the present invention. Examples of such solvates are e.g. the hydrates, alcoholates and the like.

The compound of formula (I) wherein X represents CHOH has an asymmetric carbon atom in its structure. The absolute configuration of said atom may be indicated by the stereochemical descriptors R and S. The racemate, the enantiomerically enriched mixtures and the pure enantiomers of said compound are all intended to be embraced within the scope of the present invention.

The term 'pure enantiomer' as used herein concerns enantiomers having an enantiomeric excess (e.e.) of at least 96% up to an enantiomeric excess of 100%, in particular enantiomers having an enantiomeric excess of 98% to 100%.

The most interesting compound is 2-[2-(4-chlorophenyl)-2-oxoethyl]-2,4-dihydro-4-[4-[4-(4-hydroxyphenyl)-1-piperazinyl]phenyl]-5-methyl-3H-1,2,4-triazol-3-one.

Procedures for the preparation of compounds such as the present compounds of formula (I) have been described in U.S. Pat. Nos. 4,267,179, 4,619,731, 4,791,111 and 4,931,444.

In particular, the compounds of formula (I) can be prepared from an alkyloxy derivative of formula (II) by an appropriate dealkylation reaction, e.g. in an acidic medium using a strong non-oxidizing acid, e.g. trifluoroacetic acid, or in particular a mineral acid such as concentrated hydrohalic acid e.g. hydrobromic acid, hydroiodic acid, optionally in admixture with a saturated solution of hydrobromic acid in glacial acetic acid; a Lewis acid, e.g. boron tribromide.

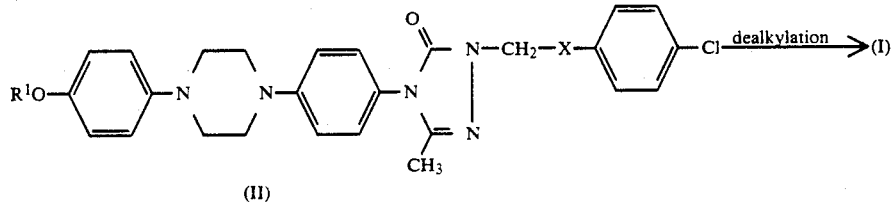

(II)

In (II) $R^1$ represents an alkyl, in particular a $C_{1-6}$alkyl group and preferably a methyl group. In the instance where hydrobromic acid is used it may be advantageous to conduct said dealkylation reaction in the presence of a bromine scavenger such as, for example sodium sulfite or hydrogen sulfite.

The compound of formula (I) wherein X represents C=O can be converted into the compound of formula (I) wherein X represents CHOH following art known reductions. For example, said reduction can conveniently be conducted by reaction with a metal hydride or complex metal hydride, e.g. sodium borohydride, sodium cyanoborohydride and the like in water or in an alcoholic medium, e.g. methanol, ethanol and the like.

The compound wherein X represents CHOH can easily be separated into its respective enantiomers by column chromatography using a chiral stationary phase such as a suitably derivatized cellulose, for example, tri(dimethylcarbamoyl)cellulose (Chiralcel OD ®) and similar chiral stationary phases.

The intermediates of formula (II) can be obtained by cyclizing an amine of formula (III) with a derivative of formula (IV) and N-alkylating the thus obtained intermediate (V) with an alkylating reagent (VI). In formula (IV) $R^2$ represents $C_{1-6}$alkyl, e.g. methyl or ethyl, and L represents a leaving group such as $C_{1-6}$alkyloxy or di($C_{1-6}$alkyl)amino, e.g. methoxy, ethoxy or dimethylamino. In formula (VI) halo represents chloro, bromo or iodo, preferably bromo.

The intermediate of formula (III) is known from U.S. Pat. No. 4,267,179. The intermediates of formula (IV) wherein L represents $C_{1-6}$alkyloxy can be prepared by addition of a $C_{1-6}$alkanol to acetonitrile and treating the

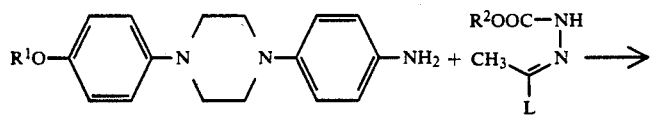

(III)        (IV)

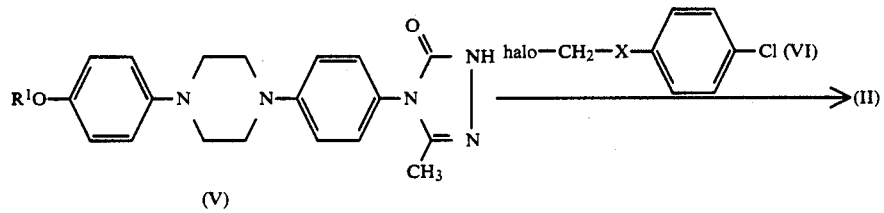

(V)

Said cyclization reaction can conveniently be conducted by stirring and heating a mixture of the reagents in an appropriate solvent such as, for example, a dipolar aprotic solvent, e.g. N,N-dimethylformamide, N,N-dimethylacetamide, 1,3-dimethyl-2-imidazolidinone, 1-methyl-2-pyrrolidinone, tetrahydrothiophene 1,1-dioxide and the like solvents. Preferably, the reaction mixture is heated at a temperature of about 100° C. and may advantageously be raised further to about 150°–160° C. The alcohol or amine which is liberated during the course of the reaction is preferably distilled off. The N-alkylation reaction of (V) with (VI) can conveniently be conducted by stirring and heating a mixture of the reagents in an appropriate solvent in the presence of a suitable base. Appropriate solvents are, for example, ketones, e.g. acetone, 4-methyl-2-pentanone, dipolar aprotic solvents, e.g. N,N-dimethylformamide, N,N-dimethylacetamide, 1,3-dimethyl-2-imidazolidinone and the like. Suitable bases are, for example, alkali metal and earth alkaline metal carbonates or hydrogen carbonates, e.g. sodium or potassium carbonate; or organic bases, e.g. triethylamine and the like bases. Preferably, the reaction is conducted with an excess of alkylating reagent ranging from about 1.5 to 2.5 equivalents at a temperature ranging from about 40° C. to about 120° C., in particular from about 45° C. to about 65° C.

Alternatively, the triazolone derivative (V) can also be prepared following the procedure described in U.S. Pat. No. 4,267,179. In said instance, the amine of formula (III) is reacted with phenyl chloroformate to yield the corresponding carbamate which is subsequently treated with hydrazine. The resulting hydrazine carboxamide is then cyclized with for example, ethanimidamide to an intermediate of formula (V).

resulting iminoether with a $C_{1-6}$alkyl hydrazinocarboxylate. The intermediates of formula (IV) wherein L represents di($C_{1-6}$alkyl)amino, can be prepared from N,N-dimethylacetamide di($C_{1-6}$alkyl)acetal by reaction with a $C_{1-6}$alkylhydrazinocarboxylate.

The compounds of formula (I) are potent and selective inhibitors of the 5-lipoxygenase enzyme both in vitro and in vivo. Inhibition of the 5-lipoxygenase enzyme effectively blocks the metabolic pathway leading from arachidonic acid to leukotrienes, which substances are known to possess a range of potent physiological effects and are presumed to be involved in a variety of allergic, anaphylactic and inflammatory reactions (Science, 220, 568–575, 1983; Science, 237, 1171–1176, 1987; N. Engl. J. Med., 323; 645–655, 1990; Drugs Future, 16, 547–558, 1991; Pharmac. Ther., 46, 57–66, 1990).

Leukotrienes $C_4$, $D_4$ and $E_4$ ($LTC_4$, $LTC_4$ and $LTE_4$) strongly induce the contraction of smooth muscles and in particular exhibit powerful bronchoconstricting properties. Further, said leukotrienes increase the vascular permeability, thus resulting in the leakage of intravascular fluid and proteins into the tissues and the formation of edema. Leukotriene $B_4$, a potent chemokinetic and chemotactic agent towards leukocytes, has been proposed as an important mediator in immediate and subacute hypersensitivity reactions and inflammatory processes (The New England Journal of Medicine, 303, 822–825, 1980; "The Leukotrienes: Chemistry and Biology", ed. L. W. Chakrin, D. M. Bailey, Academic Press, Orlando, 195–214, 1984). The above-mentioned leukotrienes are all derived from a common intermediate, 5-hydroperoxyeicosatetraenoic acid (5-HPETE) which is formed from arachidonic acid through the activity of a 5-lipoxygenase. Other lipoxygenases, e.g. 12- and 15-lipoxygenase, transform arachidonic acid

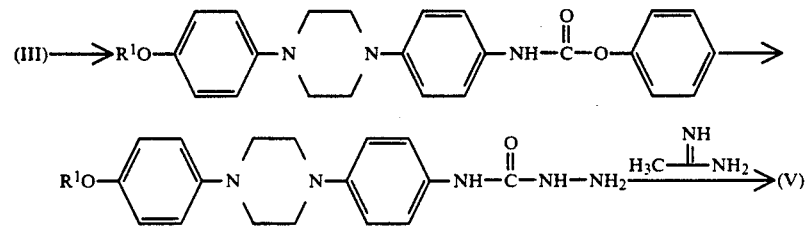

into several other mono- and dihydroxy derivatives with opposite or synergistic biological activities. Additionally, an increased release of the products of 5-lipoxygenase and 12-lipoxygenase enzymatic activity from the lesioned skin of patients with psoriasis as well as with atopical dermatitis has been reported (Prostaglandins 29, 611-619, 1985; J. Invest. Dermatol.83, 70-73, 1983; Lancet, i, 222-223, 1984).

Consequently, inhibitors of the lipoxygenase-mediated metabolic pathways of arachidonic acid, and in particular of the 5-lipoxygenase enzyme, are considered to be valuable therapeutic drugs for suppressing the above-mentioned adverse effects of leukotrienes. Associated diseases and/or disorders are, for instance bronchial asthma; allergy (N. Eng. J. Med. 323, 1736-1739, 1990; Lancet, 337, 690-694, 1991; N. Eng. J. Med. 323, 1740-1744, 1990); anaphylaxis; hyperkeratotic dermatoses, e.g. ichtyosis and psoriasis (J. Am. Acad. Dermatol. 22, 751-755, 1990; J. Invest. Dermatol. 95, 50-54, 1990); inflammatory bowel disease, e.g. ulcerative colitis and Crohn's disease; and other inflammatory reactions, e.g. (rheumatoid) arthritis and dermatitis especially atopic dermatitis. The invention gains importance by the fact that the compounds of formula (I) to be used in the present method are both potent and selective inhibitors towards the 5-lipoxygenase enzyme. Many inhibitors reported lack selectivity and concomitantly inhibit other lipoxygenases and/or cyclooxygenase, the enzyme which mediates the metabolism of arachidonic acid towards the prostaglandins. The compounds of formula (I) should not significantly inhibit soy bean 15-lipoxygenase, human platelet 12-lipoxygenase, human platelet cyclooxygenase nor thromboxane $A_2$ synthetase.

The 5-lipoxygenase-inhibiting activity is demonstrated in the "Inhibition of A23187 induced 5-lipoxygenase activity in blood of Beagle dogs"-test (example 15) (an analogous test is described in J. Pharmacol. Exp. Ther., 256, 929-937, 1991). Another important feature of the present invention is the fact that the compounds of formula (I) are orally active as can be shown in the "Inhibition of Dextran-induced edema formation in the ears of mice" test.

The main advantage of the present compounds over the prior known compounds relates to the surprising finding that remarkably higher plasma levels can be obtained with the present compounds, in particular with the compound wherein X represents C=O.

Equally interesting is the finding that said compound is metabolised mainly to an active metabolite, namely a compound of formula (I) wherein X represents CHOH.

The present invention also relates to a method of treating warm-blooded animals suffering from leukotriene-mediated diseases and/or disorders, by administering an effective 5-lipoxygenase inhibiting amount of a compound of formula (I) or a pharmaceutically acceptable acid addition salt thereof. Those of skill in the relevant art could easily determine the effective amount of 5-lipoxygenase inhibitor from the results presented hereinafter. In general it is contemplated that a suitable dose administered daily to subjects would be from about 0.1 mg/kg to about 50 mg/kg body weight, and more preferably from about 1 mg/kg to about 10 mg/kg body weight.

The subject compounds may be formulated into various pharmaceutical forms for administration purposes. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solutions, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

As appropriate compositions for topical application there may be cited all compositions usually employed for topically administering drugs, e.g., creams, gellies, dressings, shampoos, tinctures, pastes, ointments, salves, powders and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

The following examples are intended to illustrate and not to limit the scope of the present invention.

EXPERIMENTAL PART

Example 1 a) Through 400 ml of ethanol there was bubbled gaseous hydrochloric acid for 3 hours at a temperature below 10° C. At 0° C., there were added dropwise 162 ml of acetonitrile (t≦5° C.). After stirring overnight at 0° C., the precipitate was filtered off, washed with some ethanol and dried in vacuo at 40° C. under nitrogen, yielding 251 g (65%) of ethyl ethaneimidate monohydrochloride (interm. 1).

b) A mixture of 330.5 g of intermediate (1) and 2500 ml of ethanol was stirred for ½hour at room temperature. A solution of 230 g of methyl hydrazinecarboxylate in 1500 ml of ethanol, which was prepared by warning to ±50° C., was added dropwise over 1½ hour. After stirring overnight at room temperature, the reaction mixture was filtered and the filtrate was evaporated. The residue was taken up in 500 ml of dichloromethane. This solution was filtered over diatomaceous earth and the filtrate was evaporated, yielding 375.5 g (92%) of methyl 2-(1-ethoxyethylidene)hydrazinecarboxylate (interm. 2).

c) A solution of 400 g of 4-[4-(4-methoxyphenyl)-1-piperazinyl]benzenamine (prepared as described in example I of U.S. Pat. No. 4,267,179) in 1000 ml of tetrahydrothiophene 1,1-dioxide was stirred for 1 hour at 100° C. A solution of 382.8 g intermediate (2) in 200 ml of tetrahydrothiophene 1,1-dioxide, which was prepared by warming to 60° C., was added dropwise over 4 hours at 100° C. The mixture was stirred overnight at 100° C. and for 3 hours at 160° C. After cooling to 50° C., the precipitate was filtered off, washed with acetone and dried in vacuo at 60° C. under nitrogen, yielding 290 g (56%) of 2,4-dihydro-4-[4-[4-(4-methoxyphenyl)-1-piperazinyl]phenyl]-5-methyl-3H-1,2,4-triazol-3-one (interm. 3).

Example 2 a) A mixture of 5.5 g of intermediate (3) (alternatively also prepared as described in Example XIII of U.S. Pat. No. 4,267,179), 4 g of 2-bromo-1-(4-chlorophenyl)ethanone, 10 g of sodium carbonate monohydrate and 200 ml of 1,3-dimethyl-2-imidazolidinone was stirred for 1.5 hours at 80° C. The reaction mixture was poured into water. The precipitate was filtered off, washed with water and dissolved in dichloromethane. The organic layer was separated, dried, filtered and evaporated. The residue was purified by column chromatography (silica gel; CH$_2$Cl$_2$/CH$_3$OH 98:2). The eluent of the desired fraction was evaporated and the residue was triturated in ethyl acetate. The product was filtered off and dried, yielding 5.1 g (65.6%) of 2-[2-(4-chlorophenyl)-2-oxoethyl]-2,4-dihydro-4-[4-[4-(4-methoxyphenyl)-1-piperazinyl]phenyl]-5-methyl-3H-1,2,4-triazol-3-one; mp. 229.5° C. (interm. 4).

b) To a cooled (0°-5°) amount of 50 ml of a boron tribromide solution in dichloromethane 1M there was added dropwise a solution of 4.8 g of intermediate (4) in 333 parts of dichloromethane. After stirring for 2 hours at room temperature, the product was extracted with dichloromethane. The extract was washed with water, dried, filtered and evaporated. The residue was purified by column chromatography (silica gel; CH$_2$Cl$_2$/CH$_3$OH 99:1→98:2). The eluent of the desired fraction was evaporated and the residue was triturated in ethyl acetate. The product was filtered off and dried, yielding 1.4 g (30.9%) of 2-[2-(4-chlorophenyl)-2-oxoethyl]-2,4-dihydro-4-[4-[4-(4-hydroxyphenyl)-1-piperazinyl]phenyl]-5-methyl-3H-1,2,4-triazol-3-one; mp. 251.7° C. (comp. 1).

Example 3

A mixture of 25 g of intermediate (4), 350 ml of hydrobromic acid 48% and 200 ml of acetic acid was refluxed for 5 hours. The reaction mixture was stirred overnight at room temperature and was then diluted with 100 ml of water. The precipitate was filtered off, washed with water and taken up in a mixture of 700 ml of methanol and 100 ml of water. At reflux temperature, there were added dropwise 20 ml of ammonia. The reaction mixture was stirred for 5 hours at room temperature. The precipitate was filtered off, washed with methanol and dried in vacuo at 50° C. under nitrogen, yielding 20 g (82%) of 2-[2-(4-chlorophenyl)-2-oxoethyl]-2,4-dihydro-4-[4-[4-(4-hydroxyphenyl)-1-piperazinyl]phenyl]-5-methyl-3H-1,2,4-triazol-3-one; mp. 251.7° C. (comp. 1).

Example 4

To a mixture of 55 g of compound (1) in 1000 ml of N,N-dimethylformamide there was added dropwise a mixture of 8.3 g of sodium borohydride in 30 ml of water. After stirring overnight, there were added successively 50 ml of acetic acid and 1500 ml of water. The reaction mixture was left to crystallize. The product was filtered off, washed with water and dried in vacuo, yielding 54.1 g (94.7%) of 2-[2-(4-chlorophenyl)-2-hydroxyethyl]-2,4-dihydro-4-[4-[4-(4-hydroxyphenyl)-1-piperazinyl]phenyl]-5-methyl-3H-1,2,4-triazol-3-one monohydrate; mp. 264.4° C. (comp. 2).

Example 5

4.5 g of compound (2) was separated into its (+) and (−) forms by column chromatography (Chiralcel OD ®; C$_2$H$_5$OH/2-C$_3$H$_7$OH 80:20). The first fraction was concentrated to about 100 ml and the formed precipitate was filtered off and dried in vacuo at 80° C., yielding 1.64 g (36.4%) of (+)-2-[2-(4-chlorophenyl)-2-hydroxyethyl]-2,4-dihydro-4-[4-[4-(4-hydroxyphenyl)-1-piperazinyl]phenyl]-5-methyl-3H-1,2,4-triazol-3-one; mp. 251.2° C. (comp. 3).

The second fraction was treated similarly as the first, yielding 2.13 g (47.3%) of (−)-2-[2-(4-chlorophenyl)-2-hydroxyethyl]-2,4-dihydro-4-[4-[4-(4-hydroxyphenyl)-1-piperazinyl]phenyl]-5-methyl-3H-1,2,4-triazol-3-one; mp. 249.2° C. (comp. 4).

COMPOSITION EXAMPLES

Example 6

ORAL DROPS

500 Grams of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I.. The resulting solution was filled into suitable containers.

Example 7

ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining gram of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

Example 8

CAPSULES

20 Grams of the A.I., 6 grams sodium lauryl sulfate, 56 grams starch, 56 grams lactose, 0.8 grams colloidal silicon dioxide, and 1.2 grams magnesium were vigorously stirred together. The resulting mixture was subsequently filled into 1000 suitable hardened gelatin capsules, comprising each 20 mg of the active ingredient.

Example 9

FILM-COATED TABLETS

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 ml of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 mg of the active ingredient.

Coating

To a solution of 10 grams methyl cellulose (Methocel 60 HG ®) in 75 ml of denaturated ethanol there was added a solution of 5 grams of ethyl cellulose (Ethocel 22 cps ®) in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension (Opaspray K-1-2109 ®) and the whole was homogenated. The tablet cores were coated with the thus obtained mixture in a coating apparatus.

Example 10

Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration (U.S.P. XVII p. 811) and filled in sterile containers.

Example 11

Suppositories

3 Grams A.I. was dissolved in a solution of 3 grams 2,3-dihydroxybutanedioic acid in 25 ml polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°-38° C. to form 100 suppositories each containing 30 mg/ml of the A.I.

Example 12

Injectable Solution

60 Grams of A.I. and 12 grams of benzylalcohol were mixed well and sesame oil was added q.s. ad 1 l, giving a solution comprising 60 mg/ml of A.I. The solution was sterilized and filled in sterile containers.

Example 13

2% Cream 75 mg Stearyl alcohol, 20 mg cetyl alcohol, 20 mg sorbitan monostearate and 10 mg isopropyl myristate are introduced into a doublewall jacketed vessel and heated until the mixture has completely molten. This mixture is added to a separately prepared mixture of purified water, 200 mg propylene glycol and 15 mg polysorbate 60 having a temperature of 70° to 75° C. while using a homogenizer for liquids. The resulting emulsion is allowed to cool to below 25° C. while continuously mixing. A solution of 20 mg of A.I. of formula (I), 1 mg polysorbate 80 and 637 mg purified water and a solution of 2 mg sodium sulfite anhydrous in purified water are next added to the emulsion while continuously mixing. The cream is homogenized and filled into suitable tubes.

Example 14

Aerosols a) To a solution of 2.5 mg A.I. in 0.7 ml of distilled water there are added 730 μg of a 0.1N hydrochloric acid solution. After stirring for 10 minutes at room temperature, the pH of the thus obtained solution is adjusted to pH 5.5 by adding a 0.1N sodium hydroxide solution. Then there are added successively 4 mg of sodium chloride and 0.15 mg of phenylmercuric acetate and the whole is stirred to produce a complete solution. Distilled water is then added to a volume of 1.0 ml. The solution is filled in a glass bottle closed with a mechanical pump delivering 0.1 ml per puff upon administration.

b) To a solution of 2 mg A.I. in 0.7 ml of distilled water there are added 600 μg of a 0.1N hydrochloric acid solution. After stirring for 10 minutes at room temperature, 10 mg of polyvinylalcohol is dissolved in the mixture and the pH of the thus obtained solution is adjusted to pH 5.5 by adding a 0.1N sodium hydroxide solution. Then there are added successively 4 mg of sodium chloride and 2 mg of phenylethyl alcohol and the whole is stirred to produce a complete solution. Distilled water is added to produce a volume of 1.0 ml which is filled in a glass bottle closed with a mechanical pump spray delivering 0.1 ml per puff upon administration.

PHARMACOLOGICAL EXAMPLES

Example 15

Inhibition of A23187-induced leukotriene B₄ production in blood of beagle dogs-test Beagle-dogs were fasted overnight. A solution of the test compound in polyethyleneglycol (2 ml/kg) was administered directly into the stomach by oesophagal intubation. Before and at appropriate time intervals after administration of the test compound, blood samples were withdrawn from the jugular vein. These blood samples were collected on heparin. Whole blood (1 ml) was rapidly dispensed into test tubes, containing a known concentration of the calcium ionophore A23187 (25 μM), which is known to stimulate the formation of leukotriene B₄ (LTB₄). The contents of the test tubes were briefly mixed by vortexing and incubated at 37° C. for 60 min. The incubation was stopped by cooling the test tubes on ice and centrifugating the content at 10 000 g for 5 min.

The determination of LBT₄ was carried out by radioimmunoassay (RIA) using a LTB₄ assay system from Amersham Int. (England). Radioimmunoassay was carried out in TRIS HCl (50 mM, pH 8.6) supplemented with 0.1% gelatine on unextracted, appropriately diluted samples. Antibody was diluted with RIA buffer and aliquots (0.1 ml) were mixed with standard or sample (0.1 ml). ³H-labelled antigen was added, the volume was adjusted to 0.5 ml with buffer and the mixture incubated for 18-24 h. Separation of bound from free radioactive material was achieved using dextran-coated charcoal. The charcoal was spun down and an aliquot of the supernatant was counted in a liquid scintillation counter.

The median inhibition of LBT₄ (in percentage) is measured as follows. Blood samples are taken after 1 hour and 4 hours after introduction of the test compound. The amount of LTB₄ is measured in the respective samples. The inhibition is determined by comparing the latter amounts of LTB₄ with the amount of LTB₄ present in the blood before administration of the test compound. Compounds of the present invention can inhibit ionophore A-23187-induced LBT₄-production for about 80% during at least 4 hours, when administered at a dose of 1.25 mg/kg.

We claim:

1. A compound having the formula

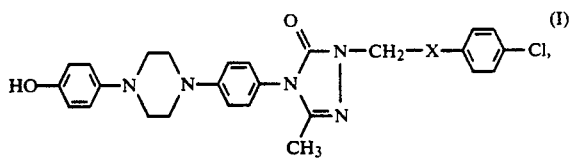

a pharmaceutically acceptable acid addition salt thereof, or an enantiomeric form thereof, wherein X represents C=O or CHOH.

2. A compound according to claim 1 wherein the compound is 2-[2-(4-chlorophenyl)-2-oxoethyl]-2,4-dihydro-4-[4-[4-(4-hydroxyphenyl)-1-piperazinyl]-phenyl]-5-methyl-3H-1,2,4-triazol-3-one or a pharmaceutically acceptable acid addition salt thereof.

3. A 5-lipoxygenase inhibiting composition comprising a pharmaceutically acceptable carrier and as active ingredient a therapeutically effective amount of a compound as defined in claim 1.

4. A composition according to claim 3 wherein said composition is in an oral dosage form.

5. A composition according to claim 3 wherein said composition is in a form suitable for topical administration.

6. A composition according to claim 5 wherein the composition is an aerosol.

7. A composition according to claim 5 wherein the composition is a cream.

8. A method of treating warm-blooded animals, suffering from leukotriene mediated diseases and disorders by administering an effective 5-lipoxygenase inhibiting amount of a compound of formula (I) as defined in claim 1.

9. A method of treating warm-blooded animals suffering from inflammatory bowel disease by administering a therapeutically effective amount of a compound of formula (I) as defined in claim 1.

10. A method of treating warm-blooded animals, suffering from hyperkeratotic dermatoses by administering a therapeutically effective amount of a compound of formula (I) as defined in claim 1.

* * * * *